United States Patent [19]

Bacehowski et al.

[11] 4,253,458
[45] Mar. 3, 1981

[54] METHOD AND APPARATUS FOR COLLECTING BLOOD PLASMA

[75] Inventors: David V. Bacehowski, Wildwood; Terrance J. Hebron, Antioch, both of Ill.

[73] Assignee: Baxter Travenol Laboratories, Inc., Deerfield, Ill.

[21] Appl. No.: 18,499

[22] Filed: Mar. 8, 1979

[51] Int. Cl.³ .............................................. A61J 1/00
[52] U.S. Cl. ................................. 128/272; 128/214 R
[58] Field of Search ................... 128/214 D; 222/107, 222/102; 264/536; 150/0.5, 8; 422/44

[56] References Cited

U.S. PATENT DOCUMENTS

| | | | |
|---|---|---|---|
| Re. 27,132 | 6/1971 | Ilg | 422/44 |
| 3,064,647 | 11/1962 | Earl | 422/44 |
| 3,142,074 | 7/1964 | Reich | 222/102 |
| 3,545,671 | 12/1970 | Ross | 233/26 |
| 3,581,943 | 6/1971 | Koenigshof et al. | 222/102 |
| 3,911,918 | 10/1975 | Turner | 128/272 |
| 3,921,630 | 11/1975 | McPhee | 128/214 D |
| 3,954,414 | 5/1976 | Samson, Jr. et al. | 422/44 |
| 4,049,033 | 10/1977 | Ralston, Jr. | 222/107 |

Primary Examiner—Robert W. Michell
Assistant Examiner—T. J. Wallen
Attorney, Agent, or Firm—Paul Flattery; John Caruso; Garrettson Ellis

[57] ABSTRACT

Blood plasma is frozen in a sealed, flexible, collapsible container which defines an inlet at one end and a shoulder portion surrounding the inlet. The container tapers from the shoulder portion to a generally flat configuration at its end opposite the one end. After the freezing step, the shoulder portion is cut away from the container to define a cut end. Thereafter, the frozen plasma may be removed from the container in frozen form by squeezing the wall of the tapered container to expel the frozen plasma out of the cut end of the container.

14 Claims, 4 Drawing Figures

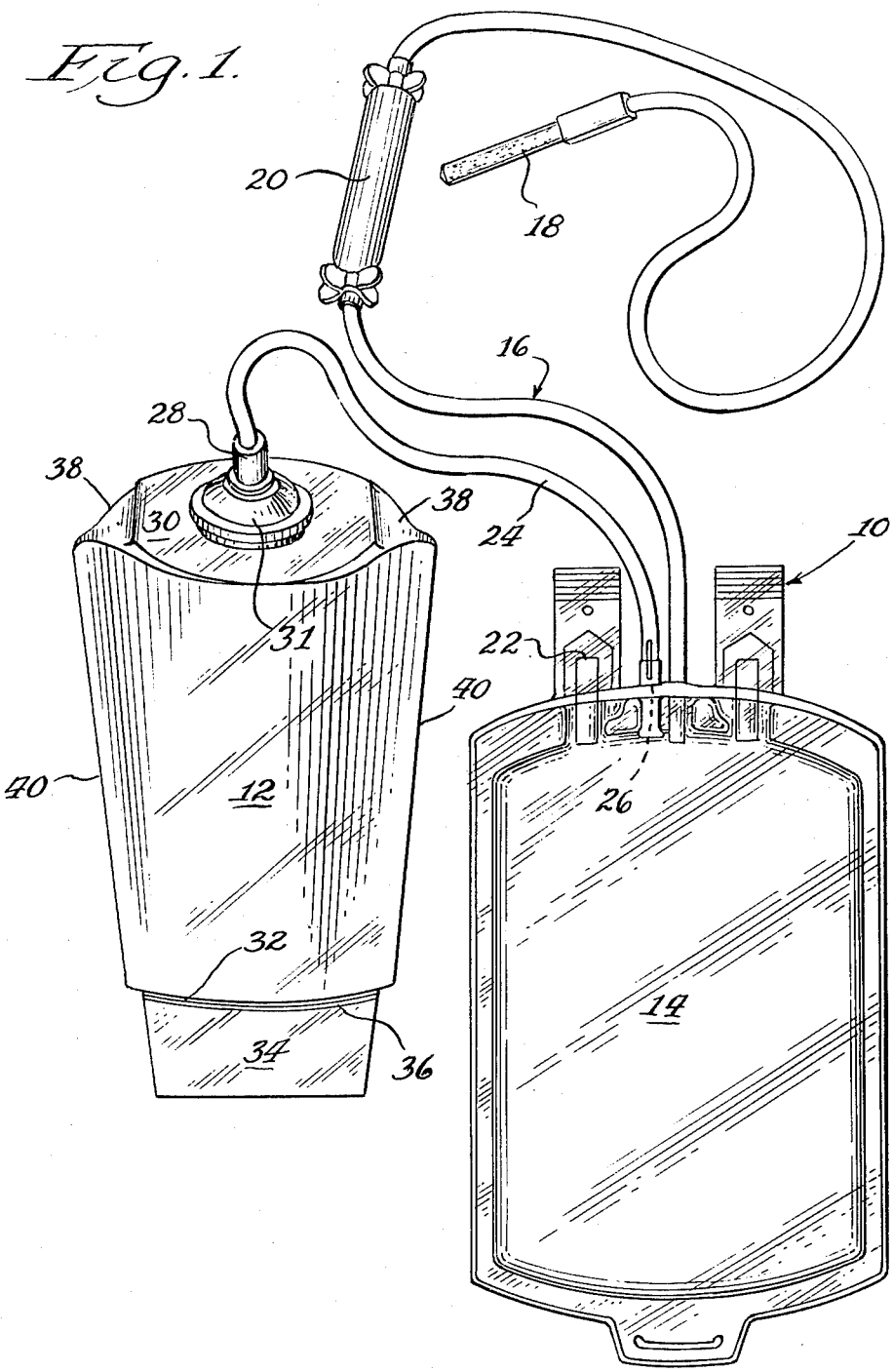

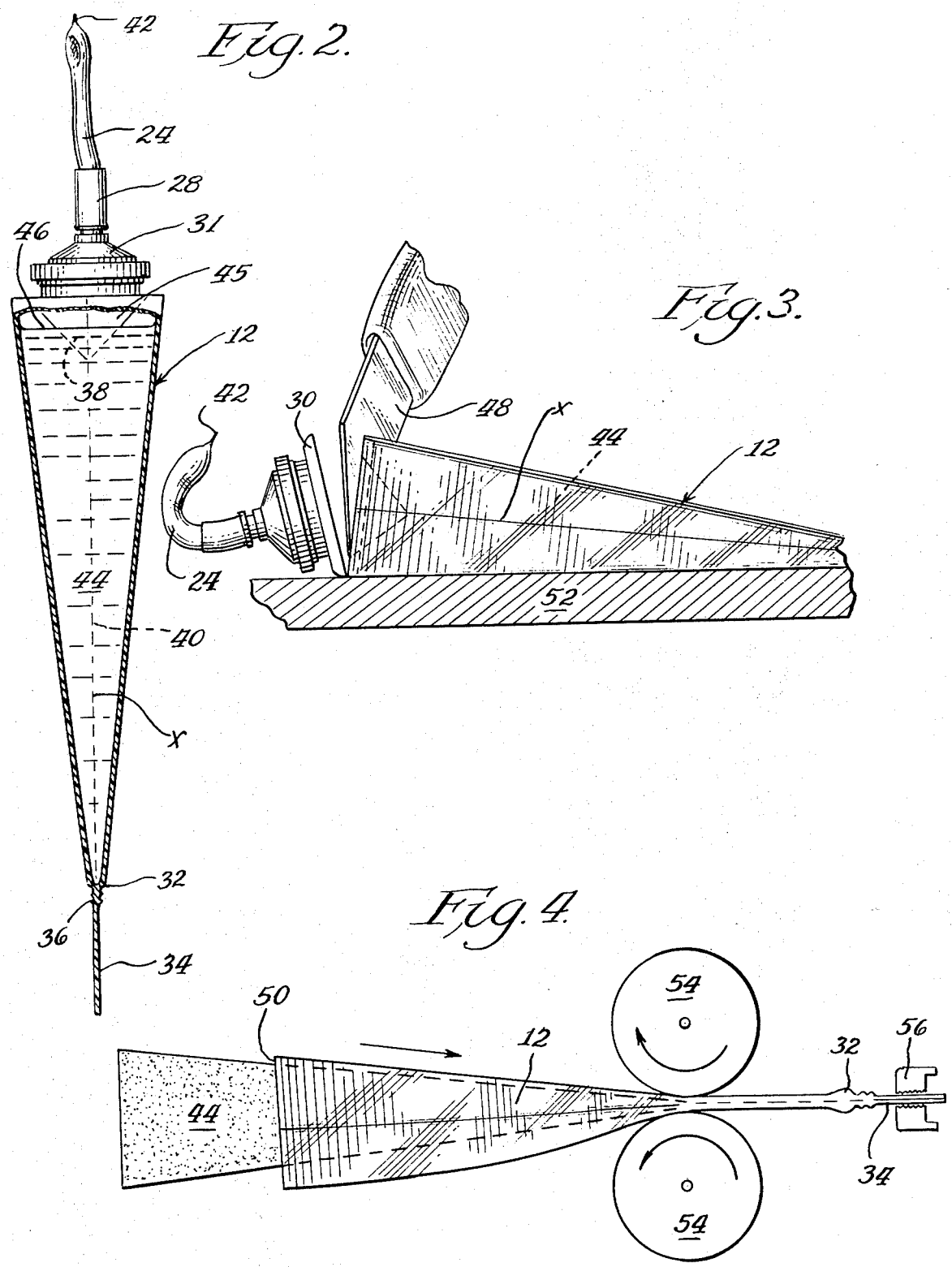

METHOD AND APPARATUS FOR COLLECTING BLOOD PLASMA

BACKGROUND OF THE INVENTION

In blood component therapy, the blood cells are often separated from the plasma by collecting the blood into a conventional, interconnected, sealed multiple bag blood collection system, followed by centrifuging the blood to separate the cells and the plasma. Thereafter, the plasma is extracted by being expressed through a sealed conduit into a "transfer pack", which is another bag of the multiple bag blood collection system. Following this, the plastic tubing is sealed and cut, to separate the plasma-containing bag, free from blood cells.

The separated bag full of plasma may then be used on a large scale basis as a raw material in the manufacture of blood components and other therapeutic items, such as serum albumin, antihemophilic factor, fibrinogen, gamma globulin, and the like.

In a typical blood plasma component manufacturing process, the plasma is pooled into a large volume container for processing to obtain the desired blood component products.

However, an inconvenience arises in that, typically, the plasma is initially collected in the multiple bag blood collection system by means of plasmapheresis or direct blood donation. The collected plasma is then typically pooled by opening the blood bags and emptying them into larger containers, which are then frozen and shipped to the blood plasma fractionation center. This provides the opportunity for contamination of the blood plasma due to exposure to the air prior to freezing, and also is quite inconvenient, requiring the opening of blood bags and pouring of them into larger containers for shipment.

At the same time, the typical polyvinyl chloride plastic used for blood bags is not a good material for freezing, since it is of significantly reduced strength at freezing temperatures, for example, $-40°$ C. and the like.

In accordance with this invention, a method and a multiple bag blood collection system are disclosed in which plasma may be effectively collected, separated from the blood cells, frozen, and then removed from its container while frozen, if desired on an automated basis. The collected blood plasma may be frozen in the bag in which it is collected, opened on a mass-produced basis, and optionally an automated basis, for removal of the frozen blood plasma for processing at the fractionation site.

DESCRIPTION OF THE INVENTION

In accordance with this invention, blood may be conventionally collected in a sealed, multiple-bag blood collection system, and centrifuged. Thereafter, the blood plasma may be expressed through a connecting tube into a connected transfer bag, separated from the rest of the blood collection system by sealing of the connecting tube and severing thereof, and frozen in the transfer bag.

The container which holds the blood plasma for freezing is a sealed, flexible, collapsible container which defines an inlet at one end and a shoulder portion surrounding the inlet. The container tapers from the shoulder portion to generally flat configuration at its end opposite to the one end.

After the freezing step, for opening of the container, the shoulder portion may be cut away to define an open, cut end. Then the frozen plasma from the container may be removed in frozen form. Because of the tapered shape of the container, the frozen, wedge-shaped plasma block may be easily squeezed out of the container by squeezing its walls, to expel the frozen plasma out of the cut end of the container.

Alternatively, in a mechanized technique, a pair of rollers may approach the plasma-containing bag from its flat end to roll the wedge-shaped block of the frozen plasma out of the cut, open end.

The various wedge-shaped frozen blocks of plasma may then be collected in a large reaction container and thawed, to begin the various fractionation steps necessary for obtaining the desired blood components.

The tapered, plasma-receiving container of this invention may initially be a part of an interconnected, sealed multiple bag blood collection system in which a flexible plastic tube communicates between the blood collection container and a blood donor container, which carries conventional tubular blood collection means.

Furthermore, conventional valve means may be provided to prevent the flow of fluid through the tubing connecting the plasma-receiving, tapered container and the donor bag until the valve is opened.

While a double-bag blood collection system is specifically shown, it is also contemplated that triple, quadruple and other multiple blood bag systems may also be utilized, in which the added blood bags may serve other conventional roles as desired, or, alternatively, other tapered plasma-receiving bags of this invention may be attached in sterile, sealed, flow-communicating manner.

In the drawings,

FIG. 1 is a plan view of an interconnected, sealed, multiple bag blood collection system in accordance with this invention, with the bags shown in collapsed configuration.

FIG. 2 is an elevational view, taken partly in longitudinal section, of the transfer bag of the multiple bag system of FIG. 1, after separation of the transfer bag from the multiple bag system, with the bag shown in its expanded, unstressed, as-molded configuration.

FIG. 3 is an elevational view of the transfer bag of FIG. 2, shown in a later stage of processing.

FIG. 4 is a partly schematic, elevational view of the container of FIG. 3 in a still-later stage of processing.

Referring to FIG. 1, the interconnected, sealed multiple blood bag collection system 10 of this invention may be similar in design to the multiple bag blood collection systems sold by the Fenwal Division of Travenol Laboratories, Inc. of Deerfield, Illinois, except for the design of transfer bag 12 in accordance with this invention.

Donor bag 14 may be of conventional design, being connected with tubular blood collection means 16, including a blood collection needle 18, shown with its cover on, and a blood sampling container 20.

The typical blood access ports 22 are provided, as well as other conventional features for a blood bag.

Transfer bag 12 is in sealingly communicating relation with donor bag 14 by means of flexible tubing 24. Conventional valve means 26 initially prevents fluid flow through tube 24 between donor bag 14 and transfer bag 12. As shown, the valve means 26 may comprise a conventional hollow cannula adapted to be manually pressed through a diaphragm which seals tubing 24 by manipulation from outside of the tubing, but other valving mechanisms may be used as well.

Tubing 24 can communicate with the interior of transfer bag 12 by means of any desired seal structure 28. Specifically, closure 28 utilizes apertured cap 31, which is attached to shoulder 30, the specific design of closure 28 being similar to that disclosed in U.S. Pat. No. 4,049,033.

In accordance with this invention, transfer bag 12 comprises a sealed, flexible, collapsible container which defines an inlet at seal area 28, and a shoulder portion 30 surrounding said inlet. Transfer bag or container 12 in its original, unstressed, as-molded configuration, tapers from the shoulder portion to a generally flat configuration at its sealed end 32.

Flat tab member 34 is then provided as a gripping member for the processing of transfer bag 12.

The end seal 36 which forms the end 32 of bag 12 may be made in accordance with the design disclosed, for example, in U.S. Pat. Nos. 4,076,063 and 4,105,730. However, as shown here, the seal 36 exhibits a slight outward curve. In the specific embodiment shown, the wall portions at the end 32 of bag 12 are brought together in a double bar seal 36 as shown in the cited patents, but not utilizing the bellows-like structure specifically illustrated in the cited patents.

At opposite ends of shoulder 30, a pair of gusset members 38 may optionally be defined, the overall container structure being similar, for example, to U.S. Pat. Nos. 4,049,033, 4,088,166 and 4,090,541, except as otherwise shown. Alternatively, the gusset members 38 may be eliminated, with shoulder 30 being correspondingly enlarged to seal the end of container 12. Also, it is generally preferred as shown, for example in FIG. 2, for bag or container 12 to exhibit, in its as-molded condition, a uniform taper from shoulder 30 to end 32.

While donor bag 14 may be made of a conventional grade of polyvinyl chloride plastic, bag 12 desirably may be made of a material which is capable of withstanding the low temperatures of plasma storage (for example, $-25°$ C. to $-80°$ C.) without becoming unduly brittle.

Polyvinyl chloride blood bags exhibit substantial brittleness at such low temperatures, to be very fragile and to often form small cracks and pinholes upon handling, or even upon exposure to vibration encountered during travel. At the same time, the material should be capable of withstanding the high temperatures of autoclaving as well.

Candidate materials for this purpose include various polyolefin materials, such as low density polyethylene and copolymers of polyethylene and polypropylene, including those containing a major amount of polypropylene.

Tubing 24, 16 may optionally be made of polyvinyl chloride since it has thicker walls and thus is stronger, or it may be made of an appropriate polyolefin material, or the like.

Bag 12 is shown in FIG. 1 in at least partially collapsed configuration, to contain substantially less volume than its normal maximum volume while valve 26 is in its initial closed position. As shown, the seven-eighths or so of bag 12 which is adjacent end 32 is in essentially flat configuration, while the area around shoulder 30 also exhibits a partial collapse.

The purpose of this is to permit blood plasma from donor bag 14 to be expressed through tubing 24 and into transfer bag 12, without the need to displace air, since the collapsed bag merely expands to receive the plasma. At the same time, a relatively small amount of air in bag 12 is generally considered desirable, to permit severing of the shoulder area 30 from the bag without the severing blade coming into contact with the plasma in bag 12.

Typically, bag 12 may be a blow-molded container which is molded in its maximum volume, uncollapsed configuration as shown, for example, in FIG. 2. In that uncollapsed configuration, the lateral side edges 40 may be generally parallel to each other, while in the collapsed configuration they diverge slightly as shown in FIG. 1.

Accordingly, as bag 12 is collapsed to expel the frozen plasma, the process is facilitated by the walls of bag 12 diverging from end 32 in the dimension illustrated in FIG. 2. The process is further facilitated by the fact that edges 40 of bag 12 also diverge from end 32 upon collapse, as illustrated in FIG. 1.

The multiple bag blood collection system of this invention may be utilized by collecting blood from a patient in conventional manner into donor bag 14. Thereafter, the blood collection system is centrifuged in the usual manner, and valve 26 is opened to provide fluid communication through tube 24. The blood plasma may then be conventionally expressed through tube 24 into transfer bag 12, while the packed red cells remain in donor bag 14.

Tubing 24 is then conventionally sealed in two places, and severed between the two seals to provide the separate bag 12 illustrated in FIG. 2, in which a fragment of tube 24 is attached to bag 12 and is closed with a sealed end 42.

Bag 12 is then placed in a freezer, preferably in the upright position, so that plasma 44 is frozen in bag 12 with air space 45 separating the upper surface 46 of the plasma from shoulder 30.

The frozen, plasma-containing bag 12 is then ready for shipment to a plasma fractionating site.

Upon arrival at the plasma fractionation site, the plasma may be pooled into a large volume container by the series of steps illustrated by FIGS. 3 and 4.

The bag 12 containing a frozen block or slug of plasma 44 may be cut with a blade 48, to cut away the shoulder portion 30 from bag 12, to define an open cut end 50. If desired, a powered band blade or any other desired mechanical cutting means may be used.

Bag 12 may rest upon a horizontal surface 52 during this operation, or alternatively it may be retained in vertical position during the cutting operation. As previously stated, it is preferable for blade 48 during the cutting operation to be spaced from the upper surface 46 of the frozen slug of plasma 44, to avoid physical contact of the blade with the plasma for purposes of aseptic handling of the plasma.

Thereafter, as illustrated in FIG. 4, the frozen plasma 44 may be removed from bag 12 in frozen form. While this may be done in any desired manner, the specific means shown in a pair of counter-rotating roller members 54 and a pair of gripping jaws 56. Jaws 56 grasp tab 34 and pull bag 12 through the counter-rotating roller members, which rotate in a direction to tend to resist pull-through of the bag. The result of this is to cause the slug of plasma 44 to be expelled from bag 12, from where it can drop into the large plasma processing container.

As can be seen, the process of cutting the shoulder portion away from bag 12 and the process of removing the frozen plasma from the transfer bag in frozen form can be easily automated on an assembly line. Surface 52 can be a conveyor member to pass bag 12 under cutting means 48. Tab 34 of the bag may be inserted through rollers 54 which may be halted or rotated in the opposite direction at that moment to facilitate the process, and tab 34 may be grasped with grippers 56, and to pull bag 12 through the rollers, to expel slug of frozen plasma 44, which may then drop into a large volume plasma collection container. Bag 12 may then be dispensed with, and jaws 56 returned for gripping and pulling another bag through rollers 54.

The above has been offered for illustrative purposes only, and is not intended to limit the invention of this application, which is as defined in the claims below.

That which is claimed is:

1. The method of freezing blood plasma in a sealed, flexible, collapsible container which defines an inlet at one end and a shoulder portion surrounding said inlet, said container tapering from said shoulder portion to a generally flat configuration at its end opposite said one end; cutting said shoulder portion away from the container after the plasma has frozen to define an open, cut end, and removing the frozen plasma from said container in frozen form by squeezing the wall of said tapered container to expel said frozen plasma out of the cut end of the container.

2. The method of claim 1 in which said container is initially a part of an interconnected, sealed, multiple bag blood collection system.

3. The method of claim 1 in which said frozen plasma is removed by passing said bag across squeeze-roller means from said generally flat, opposite end toward said open, cut end.

4. In the method of collecting blood in an interconnected, sealed, multiple blood bag system which comprises collecting donor blood into a donor bag, centrifuging said donor bag, and expressing separated blood plasma through a sealed conduit into a sealed, interconnected transfer bag, the improvement comprising, in combination: expressing said plasma through said sealed conduit into a sealed, flexible, collapsible transfer bag which defines an inlet at one end for receiving the blood plasma and a shoulder portion surrounding said inlet, said transfer bag tapering from said shoulder portion to a generally flat configuration at its end opposite to one end; freezing said plasma to solidified form in said transfer bag; cutting said shoulder portion away from the transfer bag after the plasma has frozen to define an open, cut end; and removing the frozen plasma from said transfer bag in frozen form.

5. The method of claim 4 in which said transfer bag is initially stored in its sealed configuration in the blood bag system in generally collapsed configuration so that substantially less than the maximum volume capacity of air is present within the sealed transfer bag, whereby blood plasma may be drained into said tapered transfer bag without the need to displace air.

6. The method of claim 5 in which valve means prevents the flow of fluid between said donor bag and said transfer bag until said valve means are opened.

7. The method of claim 6 in which said frozen plasma is removed by squeezing the walls of said tapered transfer bag, to expel said frozen plasma as a solid block out of the open, cut end of the transfer bag.

8. The method of claim 7 in which said transfer bag is positioned with the generally flat end opposite to said one end pointing downwardly while freezing said plasma, the upper surface of said frozen plasma in the bag being separated from said shoulder portion by an air space, to permit cutting of said shoulder portion away from the frozen plasma without physical contact between the frozen plasma and the cutting means.

9. The method of claim 8 in which the interconnected, sealed, multiple blood collection system includes two blood bags.

10. In an interconnected, sealed, multiple bag blood collection system which comprises a donor bag connected with tubular blood collection means, and at least one transfer bag sealingly communicating with said donor bag by flexible tubular means, the improvement comprising, in combination:

at least one of said transfer bags comprising a sealed, flexible, collapsible container which defines an inlet at one end and a shoulder portion surrounding said inlet, said container tapering from said shoulder portion to a generally flat configuration at its end opposite to said one end, whereby blood may be fractionated in said system and plasma frozen in said tapered transfer bag, and said frozen plasma may be easily removed from said tapered container after said shoulder portion has been cut away therefrom; valve means initially preventing fluid flow through the tubular means connecting the donor bag and the tapered transfer bag, said tapered transfer bag being in at least partially collapsed configuration to contain substantially less volume than its normal maximum volume while said valve means in its initial, closed position, whereby blood plasma may be drained into said tapered transfer bag without the need to displace air.

11. The blood collection system of claim 10 in which said tapered transfer bag is made of a plastic material capable of being autoclaved, and capable of withstanding a temperature of $-25°$ C. to $-80°$ C. without becoming unduly fragile.

12. The blood collection system of claim 11 in which said tapered transfer bag is made of a polyolefin material.

13. The blood collection system of claim 12 in which said tapered transfer bag is a blow-molded container which is molded in its maximum-volume, uncollapsed configuration.

14. The blood collection system of claim 13 in which a pair of gusset members are positioned in said tapered transfer bag adjacent opposed ends of said shoulder portion.

* * * * *